(12) United States Patent
Sabczynski et al.

(10) Patent No.: US 11,694,386 B2
(45) Date of Patent: Jul. 4, 2023

(54) IMAGE PROCESSING SYSTEM AND METHOD

(71) Applicant: KONINKLIJKE PHILIPS N.V., Eindhoven (NL)

(72) Inventors: Jörg Sabczynski, Norderstedt (DE); Manfred Mueller, Eindhoven (NL); Rafael Wiemker, Kisdorf (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 17/271,929

(22) PCT Filed: Aug. 22, 2019

(86) PCT No.: PCT/EP2019/072436
§ 371 (c)(1),
(2) Date: Feb. 26, 2021

(87) PCT Pub. No.: WO2020/043585
PCT Pub. Date: Mar. 5, 2020

(65) Prior Publication Data
US 2021/0319616 A1    Oct. 14, 2021

(30) Foreign Application Priority Data
Aug. 30, 2018  (EP) .................................. 18191721

(51) Int. Cl.
*G06T 15/08* (2011.01)
*A61B 90/00* (2016.01)
(Continued)

(52) U.S. Cl.
CPC .............. *G06T 15/08* (2013.01); *A61B 34/10* (2016.02); *A61B 90/37* (2016.02); *G06T 7/0012* (2013.01);
(Continued)

(58) Field of Classification Search
CPC ....................................................... G06T 15/08
(Continued)

(56) References Cited

U.S. PATENT DOCUMENTS 9,547,940 B1    1/2017  Sun et al.
10,398,513 B2 *  9/2019  Razzaque .............. A61B 18/20
(Continued)

FOREIGN PATENT DOCUMENTS

JP    2006187531 A    7/2006
JP    2009028077 A    2/2009
(Continued)

OTHER PUBLICATIONS

3D CT-Video Fusion for Image-Guided Bronchoscopy, William E. Higgins et al., Computerized Medical Imaging and Graphics 32 (2008) 159-173.*
(Continued)

*Primary Examiner* — Javid A Amini

(57) ABSTRACT

A System for image processing (IPS), in particular for lung imaging. The system (IPS) comprises an interface (IN) for receiving at least a part of a 3D image volume (VL) acquired by PAT an imaging apparatus (IA1) of a lung (LG) of a subject (PAT) by exposing the subject (PAT) to a first interrogating signal. A layer definer (LD) of the system (IPS) is configured to define, in the 3D image volume, a layer object (LO) that includes a representation of a surface (S) of the lung (LG). A renderer (REN) of the system (IPS) is configured to render at least a part of the layer object (LO) in 3D at a rendering view ($V_p$) for visualization on a display device (DD).

19 Claims, 7 Drawing Sheets

(51) Int. Cl.
 *A61B 34/10* (2016.01)
 *G06T 7/00* (2017.01)
(52) U.S. Cl.
 CPC .............. *A61B 2090/364* (2016.02); *G06T 2207/10068* (2013.01); *G06T 2207/30061* (2013.01); *G06T 2210/41* (2013.01)
(58) Field of Classification Search
 USPC ........................................................ 345/420
 See application file for complete search history.

(56) References Cited

U.S. PATENT DOCUMENTS

| | | | |
|---|---|---|---|
| 2012/0219200 A1* | 8/2012 | Reeves | G06T 5/30 382/131 |
| 2012/0288173 A1* | 11/2012 | Rai | G06T 7/20 382/128 |
| 2014/0347353 A1 | 11/2014 | Popovic | |
| 2018/0161102 A1 | 6/2018 | Wei | |
| 2019/0262076 A1* | 8/2019 | Brown | A61B 34/10 |
| 2020/0046431 A1* | 2/2020 | Soper | A61B 1/2676 |
| 2020/0211181 A1* | 7/2020 | Govari | G06T 15/08 |
| 2020/0352516 A1* | 11/2020 | Entenberg | A61B 5/418 |
| 2020/0375666 A1* | 12/2020 | Murphy | G02B 27/017 |
| 2021/0256716 A1* | 8/2021 | Siewerdsen | G06T 7/11 |
| 2021/0378750 A1* | 12/2021 | Navab | A61B 34/10 |

FOREIGN PATENT DOCUMENTS

| | | |
|---|---|---|
| WO | 2011128792 A2 | 10/2011 |
| WO | 2016070109 A1 | 5/2016 |

OTHER PUBLICATIONS

International Search Report and Written Opinion of PCT/EP2019/072436, dated Oct. 24, 2019.
Higgins, William E. et al "3D CT-Video Fusion for Image-Guided Bronchoscopy" Computerized Medical Imaging and Graphics, vol. 32, No. 3, Dec. 2007, pp. 159-173.
Ueno, Junji et al "Three-Dimensional Imaging of Thoracic Diseases with Multi-Detector Row CT", Journal of Medical Investigation, vol. 51, No. 3-4, Aug. 2004, pp. 163-170.
W. R. Webb, "Thin-section CT of the secondary pulmonary lobule: Anatomy and the image—the 2004 Fleischner Lecture," Radiology, vol. 239, No. 2, pp. 322-338, 2006. Abstract Only.
Mangold, Klaus et al, "The physics of near-infrared photography," Eur. J. Phys., vol. 34, No. 6, pp. S51-S71, 2013.
Alvarez, Pablo et al "Modeling lung deflation during video-assisted thoracoscopy surgery for the localization of small nodules", EUROMECH Colloquium 595, Aug. 2017, France.

* cited by examiner

IMAGE PROCESSING SYSTEM AND METHOD

CROSS-REFERENCE TO PRIOR APPLICATIONS

This application is the U.S. National Phase application under 35 U.S.C. § 371 of International Application No. PCT/EP2019/072436, filed on Aug. 22, 2019, which claims the benefit of European Patent Application No. 18191721.2, filed on Aug. 30, 2018. These applications are hereby incorporated by reference herein in their entirety.

FIELD OF THE INVENTION

The invention relates to an image processing system, to an image processing method, to a computer readable medium and to a computer program element.

BACKGROUND OF THE INVENTION

Lung surgery is becoming more and more minimally invasive. For different kinds of intervention, open thoracotomy is no longer necessary. This reduces greatly patient discomfort as open thoracotomy entailed considerable incisions. Instead, in "Video Assisted Thoracoscopic Surgery" (VATS), a type of minimal invasive surgery, an endoscope is introduced through a small incision into the thoracic cavity. The surgeon is then provided with video images transmitted from an endoscope to a monitor, while operating with instruments, which may be introduced through additional, small incisions.

VATS may be used for oncologic procedures, e.g. for removal of a malignant neoplasm (lobectomy, segmentectomy, wedge resection etc.), but can be used also for other reasons, e.g. volume reduction surgery for treating severe COPD or other.

One issue with lung surgery, both open thoracotomy and minimally-invasive VATS, is lung deflation. Usually, the lungs fill the thoracic cavity. They are not able to inflate themselves and expand only when the volume of the thoracic cavity increases. Under normal conditions, pressure inside the lungs is always higher than the pressure inside the pleural space between thorax and lung. When the thorax is opened by applying the said incisions, the pressure inside the thoracic cavity becomes the same as the pressure inside the airways and the elastic lung tissue collapses. Therefore, during surgery, the lung is much smaller than before the operation.

In many other surgical disciplines (neurosurgery, orthopedics, spine surgery, ENT surgery and many more) as well as in interventional radiology, technical methods for guiding the surgeon or interventional radiologist to a target have been developed. These navigational methods may rely either on pre-operative imaging (e.g. CT, MRI, 3D X-ray, PET, etc.) or intra-operative imaging (ultrasound, X-ray, etc.). In these methods, when pre-operative imaging is used, the anatomy of interest does not in general change markedly between imaging and intervention so as to compromise the accuracy of navigation.

Due to deflation, the lung undergoes large-scale deformation between pre-operative imaging and during the intervention. This makes navigation based, for example, on pre-operative CT difficult.

At least in open surgery, surgeons can palpate the lung to find a lesion. In VATS, this is no longer possible.

SUMMARY OF THE INVENTION

There may therefore be a need for an alternative system or method to support lung imaging or lung intervention.

The object of the present invention is solved by the subject matter of the independent claims where further embodiments are incorporated in the dependent claims. It should be noted that the following described aspect of the invention equally applies to the image processing method, the image processing system, to the computer program element and to the computer readable medium.

According to a first aspect of the invention there is provided a system for image processing, comprising:

an input interface configured to receive i) at least a part of a 3D image volume based on image data of a lung of a subject acquired by a first imaging modality and ii) a second image of the lung acquired by a second imaging modality during a lung intervention;

a layer definer configured to define, in the 3D image volume, a layer object that includes a pattern representative of a lung vessel and/or a septum as a representation of a surface of the lung;

a renderer configured to render at least a part of the layer object in 3D at a rendering view for visualization on a display device, and a matcher configured to instruct the renderer to render the view of the layer object so as to match the second image based on the representative pattern.

According to one embodiment, the rendering is confinable to at least a part of the layer object or wherein the renderer is configured to render the layer object with a higher contribution than non-layer elements of the volume.

It has been found that certain patterns on the lung's surface such as vessels or structures that stem from septa underneath the outer surface are characteristic for a certain spatial view on the lung. Such patterns are also referred to as "representative patterns" hereinafter. Also, the pattern has been found to be largely topologically invariant under deformation caused by deflation of the lung. By confining or at least emphasizing the layer object, contrast can be better concentrated rather than stretching same to cover tissue that is situated too deep to make a significant visual contribution. Also, by using the penetration depth, the structures that do contribute to the visual appearance of the lung can be further harnessed. In sum, a more reliable image-based navigation is achieved that is of particular benefit for lung interventions. Imagery of a lung in inflated and deflated state can be reliable and robustly matched thus furthering the reliability of lung-image-based navigation.

According to one embodiment, the layer definer is configured to define a thickness of the said layer based on a penetration depth of an interrogation signal of the second imaging modality. This second interrogation signal is used for acquiring a second image of the lung or of another similar lung by exposure to the second interrogating signal.

Second interrogating signal exposure may occur from the outside, the second interrogating signal propagating through an opening in the patient's skin towards the lung. Alternatively, exposure may occur from inside the patient, after a probe of the imaging apparatus has been introduced through an opening into the patient and suitably positioned in respect of the lung.

Preferably, the first and second imaging modalities or apparatus are both operable to acquire imagery of a lung of the same patient but in some alternative embodiments, the first imaging modality or apparatus was used to acquire the pre-operative image from one patient's lung whilst the intra-operative second image is acquired by the second imaging modality or apparatus of a lung of another patient.

According to one embodiment, the layer definer is configured to define the layer object based at least on lung tissue segmentation sub-volume.

According to one embodiment, the layer definer is configured to define the layer object based on a tangent surface to a pre-defined point of a lung segmentation sub-volume and an extension of the tangent surface along a local normal direction of the tangent surface.

The layer object includes a pattern representative of a lung vessel and/or a septum. Then, according to an embodiment, the renderer is configured to render the pattern with color- or grey value encoding different from its surrounding in which the pattern is at least partly embedded.

According to one embodiment, the renderer is configured to set a transparency of the rendered layer object, so as to occlude, given a rendering position, an opposed, distal portion of the layer object or wherein the layer object is pruned to exclude the distal portion from being rendered. The rendering position describes, in particular, the position of a conceptual camera from which the rendering is performed by casting geometrical rays through the volume and onto an image plane on which the rendered view is projected as a (2D) image.

According to one embodiment, the system includes a display device interface configured to effect displaying on the display device DD, or on two display devices, a visualization of the rendered view and of the second image.

According to one embodiment, the second imaging apparatus is capable of conferring contrast in the second image based on at least one pre-defined material present in the lung, the renderer configured to color- or grey-value encode a portion in the view that corresponds to the material.

According to one embodiment, the system includes at least one of the first or second imaging modality or apparatus and or the at least one display device.

According to a second aspect there is provided a method of image processing, comprising the steps of:

receiving i) at least a part of a 3D image volume of a lung of a subject based on image data acquired by a first imaging modality and ii) a second image of the lung acquired by a second imaging modality;

defining, in the 3D image volume, a layer object that includes a a pattern representative of a lung vessel and/or a septum as a representation of a surface of the lung;

rendering at least a part of the layer object in 3D at a rendering view for visualization on a display device so as to match the second image, based on the representative pattern.

According to one embodiment, the rendering is confinable to at least a part of the layer object or rendering of the layer object is done with a higher contribution than non-layer elements of the volume.

According to a third aspect there is provided a computer program element, which, when being executed by at least one processing unit, is adapted to cause the processing unit to perform the method as per any one of the previously mentioned embodiments.

According to a fourth aspect there is provided a computer readable medium having stored thereon the program element.

The proposed system provides supports navigation and orientation in lung interventions. Despite the large scale deformation of the lung pre-op and intra-op, the proposed system allows reliably relating pre-operative image information, e.g. the position and extent of a lesion, to the intra-operative situation.

The proposed system and method may be used for different types of lung interventions, such as open surgery through thoracotomy as well as sternotomy or minimally-invasive surgery (such as VATS), with particular benefit for lung tumor imaging or lung intervention.

Definitions

In the following distinction will be made between physical objects and their representation in the respective imagery. For instance, the lung as a physical entity may be represented by a voxel subset, e.g., a sub-volume, in the total volume. The sub-volume may represent the lung. Such representative voxel subsets or sub-volumes may be referred to herein as "objects", for instance, a "lung object" is an image representation of the lung in terms of the voxel subset or sub-volume. A vessel object is hence a representation in the volume V of vessel and so forth. A similar convention may be used for pixel objects in 2D images.

"Interrogating signals" are those issued by the first and second an imaging modality or apparatus to gain knowledge about a certain anatomy. The signal is issued by a suitable transmitter or source to then interact with tissue. After or during such interaction, the signal is detected by a detector device and processed into imagery. The imagery may reveal details about the anatomy. The interrogation signals may be a form of radiation such as electromagnetic but other signal types such as ultrasound are also envisaged. Exemplary radiation-based interrogating signals for imaging purposes include X-ray, radio frequency pulses, gamma radiation, visible or infrared light, or others.

"3D", "2D" is shorthand for spatial three-dimensionality and two-dimensionality, respectively.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
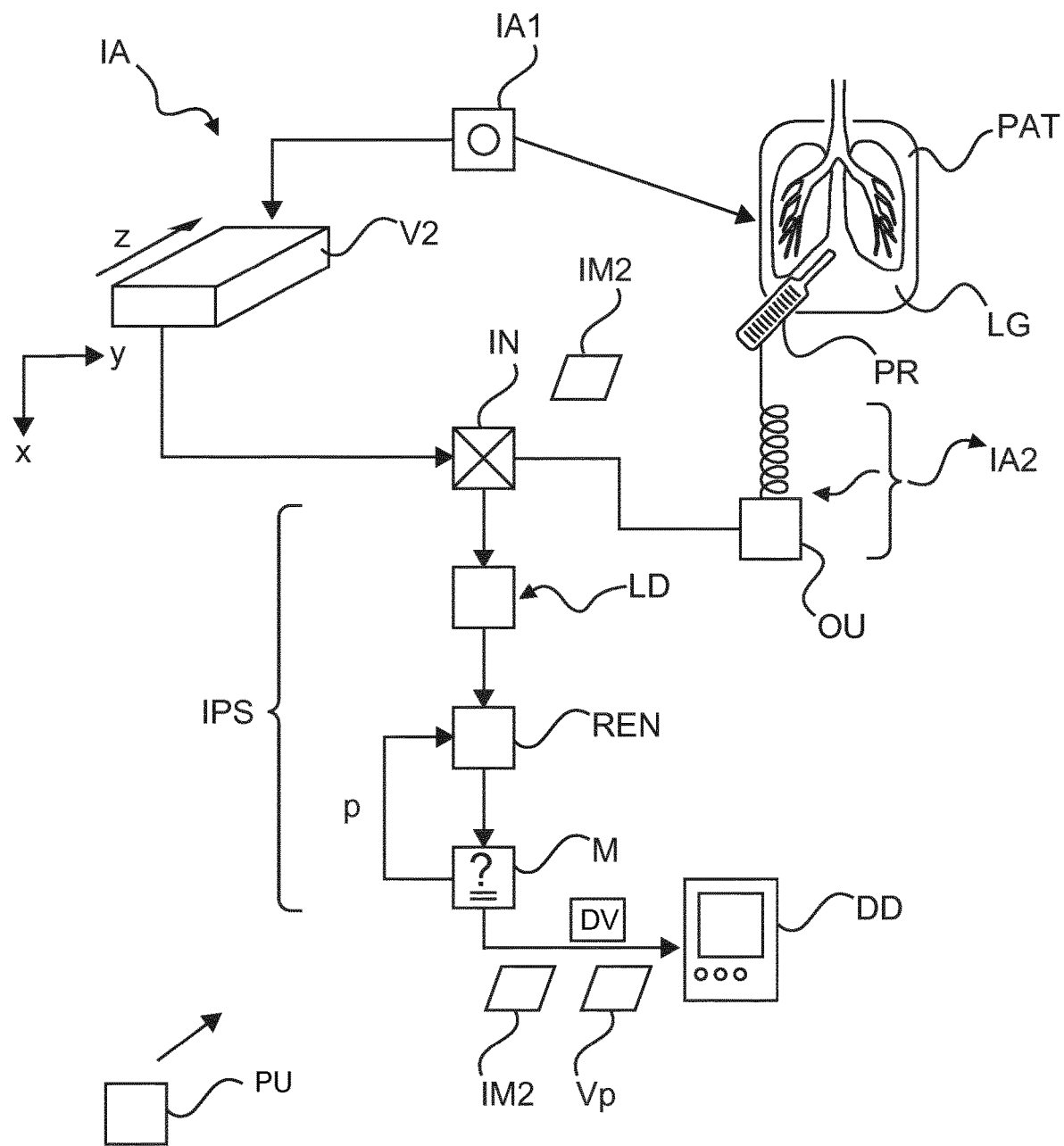
FIG. 1 shows a schematic block diagram of an imaging arrangement.

With reference to FIG. 1, there is shown a schematic block diagram of an imaging arrangement IA as envisaged herein in embodiments.

The imaging arrangement IA is in particular configured for imaged-based support of lung LG interventions. To this end, the imaging arrangement IA includes two imaging modalities IA1 and IA2, preferably different.

One of the imaging modalities IA1, also referred to herein as the pre-operative imaging modality IA1, is configured to acquire a preferably volumetric VL image set of a human or animal patient PAT. The volumetric imagery VL includes in particular a representation of the region of interest ROI which includes in particular lung LG. When referring to lung LG herein, this should be construed as a reference to either the left lung, the right lung or to both. Contrast agent may be administered to the patient prior or during imaging with the pre-operative imager IA1.

The second imaging modality IA2, referred to as the intra-operative imaging modality IA2, is configured to acquire an image IM2 during the lung LG intervention.

Broadly, the imaging arrangement is configured to support VATS or similar lung interventions. More particularly the imaging arrangement IA supports an operator (that is, the person carrying out the intervention) to navigate the lung during the intervention, to find in particular a specific lung portion such as a lesion or other portion. The arrangement IA may support said navigation based in particular on the pre-operative imagery VL and/or intra-operative imagery obtained during the intervention.

In one embodiment, the pre-operative imager IA1 is configured for transmission imaging with ionizing radiation. One particular embodiment of this is computed tomography imaging (CT), including Cone Beam CT, fan beam or any other variant. Instead of transmission imaging, emission imaging is also envisaged in alternative embodiments, such as PET (positron emission tomography) or SPECT (single-photon emission computed tomography). However, imaging modalities that employ non-ionizing radiation are also envisaged such as MRI (magnetic resonance imaging) or other.

In CT, mainly envisaged herein in embodiments, the volumetric image data VL is reconstructed from image data, in particular projection imagery, acquired of the patient PAT. The projection imagery is acquired in rotational fashion by having an x-ray source and/or an x-radiation detector rotate around at least the region of interest, in this case the lung LG. During the rotation, projection imagery is acquired of the ROI from multiple directions. To do this, the X-ray source traces out, a not necessarily complete arc, around the region of the upper torso of the patient where the LG are located. Arcs subtending 180° or less are usually sufficient for this. Mathematical reconstruction algorithms such as filtered back-projections or others are then used to process the projection imagery into slice images that are located in the examination region. The examination region is the portion of space where the region of interest is located during imaging. By advancing the patient or the x-ray source transversely along a longitudinal axis, the imaging axis Z, to acquire different sets of projection images are acquired from such a plurality of slice images in different planes can be reconstructed to so form the volumetric image data VL. The patient's longitudinal axis is in general aligned with said imaging axis Z. The volumetric image date VL, also referred to herein the image volume, includes a 3D image representation of the lung LG.

Image values of the imaging volume VL are organized in voxels. Each voxel is defined by an image value and a 3D position in space that corresponds to a point in the examination region and hence to a point within the patient PAT. Each image value encodes the manner of interaction with the interrogating signal used in the imaging modality. For CT or similar, the interrogating signal is an X-ray signal that passes through the patient and interacts with matter therein and is then detected by the detector in the projection imagery and then processed as described into voxel values. In this case, the image value at a given voxel may be related to an amount of attenuation experienced by the interrogating X-ray signal. In other imaging modalities, the interrogating signals are different and the image values represent other interaction principles. For instance, in MRI the interrogating signals are formed from radiofrequency pulses, in emission imaging, the interrogating signals are formed from gamma radiation emanating from decay events of tracer substances in the patient's body.

Turning now briefly to the intra-operative imaging modality IA2, this is envisaged in particular as an endoscopic imaging unit. This comprises a probe PR introducible into the patient. The endoscopic imaging unit IA2 may further comprise an operating unit OU communicatively coupled in a wired or wireless connection with the probe PR. The probe PR is introduced into the patient through a, preferably small, incision, in the patient's chest to access lung LG. More specifically, probe PR is advanced into the thoracic cavity where the lung is located (more of this below at FIG. 2). The endoscopic imaging unit may then operate to acquire images of the interior of the patient, in particular of the lung LG. Preferably non-ionizing radiation such as visible light, infrared (IR) light, or near-infrared (NIR) light or others is used. For instance, light signal, such as visible light, is used as the interrogating signal for the second imaging modality IA2. The light signal is emitted by the probe and interacts with lung tissue. The light is then at least partly reflected back and registered at the probe by a suitable light detector device in the probe. Some of the light may be absorbed by the issue. The light detector device may also be arranged separate and away from the probe PR.

The reflected off light signals as detected at the detector device may then be forwarded to a processing unit in the operating unit OU to be processed into imagery that can be displayed on a display device DD in preferably real time. In this manner, a stream of frames is generated acquired at a suitable sampling frequency. The intra-operative imagery is in general not 3D as opposed to the volumetric imagery obtained by the CT or pre-operative imaging device and is hence arranged into a two dimensional array of pixel values. Again, each pixel value is arranged at a corresponding location in an imaging plane (addressable by rows and columns x,y) whilst the image value describes the manner of interaction with the interrogating signal such as the visible light, IR, NIR etc. In particular, the amount of back-reflected light is registered and quantified as a respective image value.

It will be appreciated that, depending on characteristics (such as frequency) of the light used by the endoscope IA2, the interrogating light has a certain penetration depth d to penetrate into the lung tissue. The detected light may hence supply also structural information situated d units deep underneath an utmost surface S of the lung LG. It will be understood, that instead of as endoscopic equipment, the second imaging modality IA2 may be arranged as an ultrasound (US) imager, or other imaging modality.

The imaging arrangement IA comprises an image processing system IPS that can be implemented in hardware or software. For instance, the image processing system may run on one or more processors PU such as general purpose computers, servers, or microcontrollers. The one or more processors PU may be communicatively coupled with the intra-operative IA2 and/or pre-operative imaging modality IA1. The image processing system IPS is configured to process both the pre-operative imagery VL and the intra-operative imagery IM2. Broadly, and as is proposed herein, the intra-operative imagery IM2 acquired by the endoscope IA2 at a certain instance corresponds to a given view on the lung tissue LG. This view is then matched by a matcher M to a corresponding view on the imaging volume VL and hence on the lung as represented by the volume VL.

The corresponding view is computed by a renderer REN. Specifically, the view rendered by the renderer REN corresponds, in 3D space, to the view provided by the intraoperative imager IA2. The so computed view VP is an image that is then preferably displayed together with the intra-operative imagery IM2 on the same display unit DD in different panes or on two or more separate display devices DD, preferably arranged in the operating theatre.

Figure 2A:
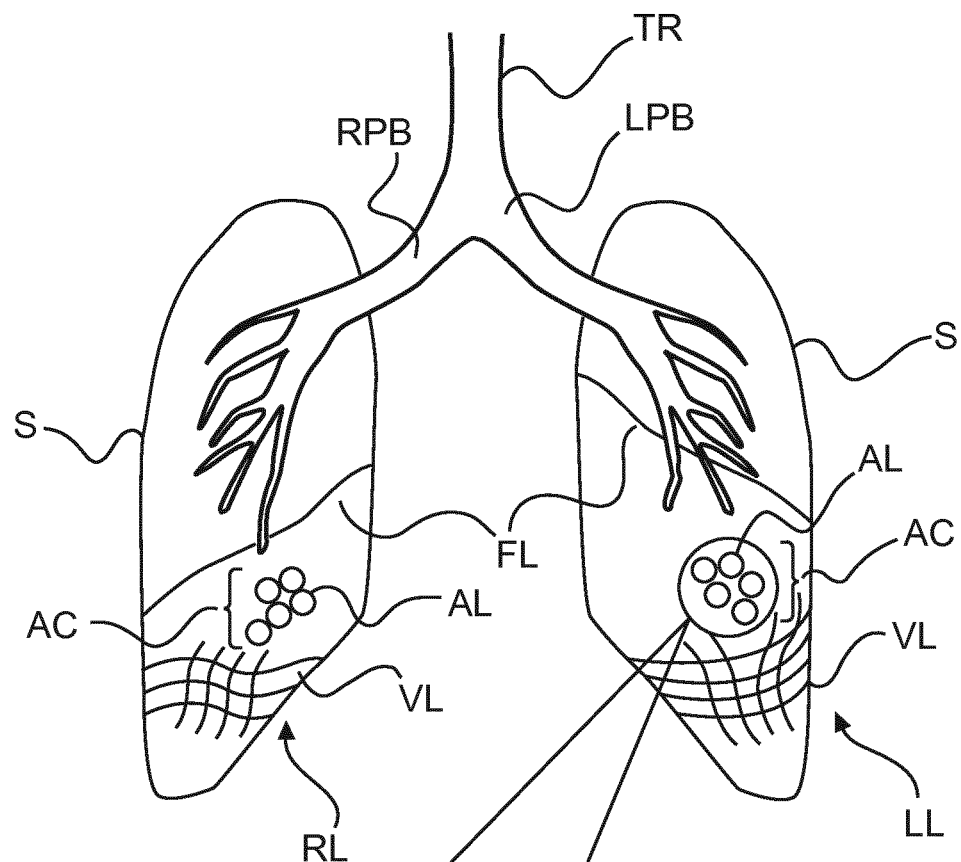
FIG. 2 shows a sagittal view of parts of a human or mammal respiratory system including the lungs.
Figure 2B:
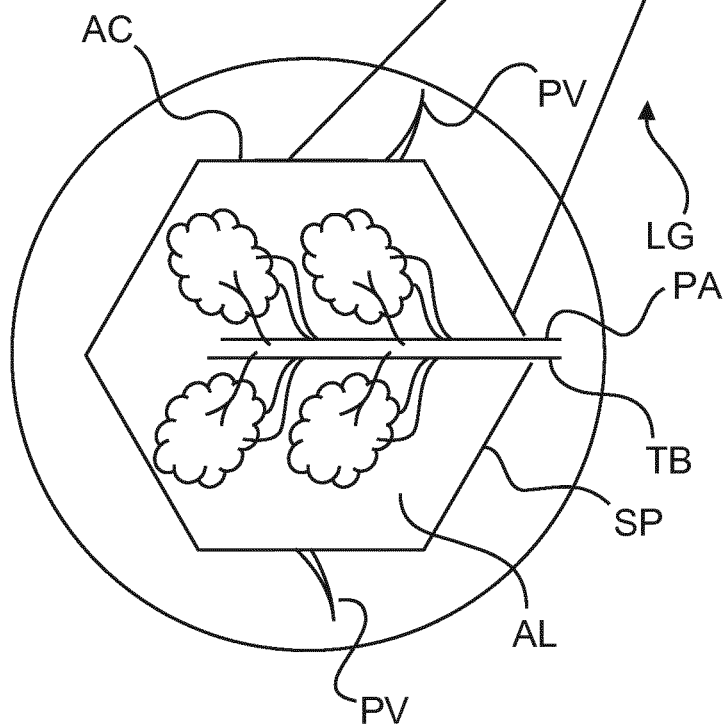

Before explaining in more detail the operation of the imaging arrangement IA and, in particular operation of the imaging processing system IPS, reference is first made to FIGS. 2A, B that relate some aspects of the lung LG anatomy which are exploited herein. FIG. 2A is a sectional view in sagittal plane through a human or animal lung LG.

The lung LG comprises left lung LL and right lung RL. The lung is part of the respiratory system. The lung is instrumental in gas exchange where carbon dioxide generated by the metabolism is expelled whilst blood is replenished with oxygen to be then supplied to various sites throughout the body.

The respiratory system includes in particular a trachea TR through which air is drawn in. The trachea TR branches into the right primary bronchus RPB and the left primary bronchus LPB. Each of the primary bronchi branches are terminates into a fine network of air sacks or alveoli AL where the gas exchange is taking place. The human lung LG is structured by fissure lines FL. The human left lung LL is structured by a single fissure lines FL into two lobes whilst the human right lung RL is structured by two fissure lines FL into three lobes. The lungs LR, LL are arranged in the thoracic cavity. The thoracic cavity is the space defined by the pleura, a membrane lining the upper part of the thoracic cavity, and the diaphragm at its lower. Normally, the lungs are in an inflated state as they are slightly pressurized by the air inside the lungs, relative to the surrounding pressure in the thoracic cavity.

The alveoli AL in the left or right lung into which the respective main branches RPB, LPB terminate confer the characteristic spongy texture of the lung tissue. Each lung RL, LL comprises an outermost surface S. This outermost surface S may in principle be touched by the operator when performing an open tracheotomy also envisaged herein in embodiments. The alveoli AL are enmeshed by a fine network of (blood) vessels including arteries and veins. The arteries are operative to conduct oxygen rich blood away from the alveoli into the system to other organs whilst the veins provide the oxygen depleted and carbon dioxide rich blood to the alveoli to affect the gas exchange. The air drawn in through the trachea TR ends up in the small air enclosures formed by the alveoli. The gas exchange occurs by diffusion through the thin skin of the alveoli and into the vessels, in particular into the capillaries of the pulmonary arteries and pulmonary veins.

The structuring of the alveoli is such that clusters emerge that are called second pulmonary lobules. Each such lobule is made of a plurality of sub-clusters of alveoli called acini. Each one of the acini may comprise about 5-12 alveoli. A schematic cross section of such a secondary pulmonary lobule SPL is shown in the inset close-up FIG. 2B in enlarged fashion. Each SPL is fed by pulmonary veins PV and pulmonary arteries PA. The alveoli in each of the acini are terminal branches of terminal bronchioles TB. The global shape of SPL is that of an irregular polyhedron delineated by walls of connecting tissue called interlobular septa SP. These contain the pulmonary veins and also lymphatic components. The SPL form the largest lung unit in which all airways participate in gas exchange. The global size of an SPL is about 1-2.5 cm across.

The connective tissue of the septa SP form in part (not non-necessarily hexagonal) a honeycomb structure on the outer surface of the lung tissue S. This network of irregular shaped polygons is visible optically, to the naked eye, when one looks at the lung LG in an open tracheotomy or when the lungs are removed from the body. However, the septa do not actually raise the surface S but lie deeper below, yet still visible to confer the (honeycomb) network structure of irregular shaped polygons as mentioned.

The network of vessels enmeshing the alveoli form a crisscross pattern, especially those that lie at the outer surface S of the lung. Some of the vessels that contribute in expressing this pattern are situated such that they slightly raise the outer surface S to give it a partly relieved structure.

It has been observed by the inventors that the pattern conferred by the septa SPL or by the vessel network pattern, in particular both patterns together, are characteristic for a given view. Either or both of these patterns can be hence thought of as a visual signature for a given view onto the lungs LG from a given spatial direction. The patterns may be expressed by suitably image structures in the intra-operative and pre-operative imagery. It is proposed herein to exploit these signature pattern(s) to find the corresponding view $V_p$ onto the image volume VL. The view $V_p$ on the volume VL is found and rendered by renderer REN. The view $V_p$ corresponds to a given optical image IA2 supplied by the intra-operative imaging modality IA2. The view $V_p$ will be referred to in the following simply as "image $V_p$", with p being a rendering parameter as will be explained in more detail below. The pattern may in particularly be formed by superficial vessels, that is, the ones that are located sufficiently close to the lung's outer surface S to imprint the relieved structure thereon.

It has been observed that the patterns can be captured not only by optical imagery as supplied by the endoscope but also by CT slice images acquired at a suitably dimensioned slice thickness of about 100 μm. In particular, the vessels close to the lung surface S are clearly detectable in high-resolution images of the lung. The interlobular septa themselves are relatively thin (about 100 μm thickness) and are thus more difficult to see directly in high-resolution CT. In cone beam CT the resolution is improved and the structures may be better defined.

In particular, the observed pattern of vessels and/or lobular septa are suitable for navigation purposes in image structure matching because they have been found to be essentially topologically invariant under the deformation of the lung. More specifically, during the intervention the lung is substantially deformed as is deflates during the intervention, in particular when the incision in the chest is applied to allow passage of the probe PR.

A robustness of the proposed image-based matching between intra-operative and pre-operative imagery is enhanced herein by recognizing that the interrogating signal of the intra-operative image modality has a certain penetration depth. In exemplary embodiments, the visible, IR or NIR light penetrates the lung tissue down to a certain depth d that depends on the frequency of the light. It is proposed herein that the image processing system IPS takes this penetration depth d into account when rendering the view on the image volume to be matched with the intra-operative imagery.

It has been found that such a rendering confined to a layer object LO that corresponds to this penetration depth in the volume VL increases the robustness of the matching and hence provides better navigation for at least two reasons: first, image contrast in the rendering is concentrated onto a region that matters, namely the layer of the lung having the thickness of the penetration depth. Otherwise, image contrast may be uselessly wasted on image structures that are not visible anyway in the preferably non-ionizing radiation based intra-operative imager IA2. Second, robustness of the image matching operation can be increased because by recognizing the tissue penetration depth, the imagery supplied by the intra-operative imaging modality may be more fully used as structures away from the outermost layer S but still within the penetration depth layer at distance d from the outer surface S still contribute to the imagery supplied by the intra-operative imaging modality. The matching can be extended to not only account for image structure that correspond to the surface, but also to structures that represent lung tissue d unit deep down from the surface S.

Furthermore, the rendering procedure can be sped up because fewer voxels, namely the ones in layer object LO (see FIG. 3 for details), need to be processed and the rendering can be terminated earlier. There is no need to process voxels deeper in the volume beyond the layer L.

With continued reference to the block diagram of FIG. 1, the image processing system IPS includes a layer definer LD that defines or identifies, preferably by image processing, a layer object LO in the total volume VL. The layer object LO, or sub-volume, has a geometric structure of a layer L or "shell" of thickness d. Topologically speaking, and in rough approximation, the defined layer object LO with thickness d may be thought of as a hollow ellipsoid embedded in the 3D volume VL.

The layer object LO represents lung tissue LG that includes in particular its outer surface S but also represents lungs structures information that are situated deeper from the surface S up to the distance d given by the penetration depth of the intra-operative imaging modality IA2. In this manner a hollowed-out volume VL is formed as the lung layer object LO.

Broadly then, during operation of the IPS, the intra-operative imagery IM2 and at least a part of the pre-operative image volume VL is received at an interface IN, not necessarily at the same time. The layer identifier LD then identifies the layer object LO by segmentation or otherwise in the volume VL that corresponds to the outer surface S and tissue up to d units deep from the outer layer S of the lung LG. Given the intra-operative imagery IM2, matcher M finds the view $V_p$ on the layer object LO that corresponds to image structures in a current intra-operative imagery IM2. This matching can be done by changing rendering parameters p below until such a match is found. This will be explained in more detail below. The match is attempted and evaluated by matcher M and once a match is found the corresponding view $V_p$ is output as an image preferably together with the current intra-operative image IM2. The image values of the two images $V_p$, IM2 are then forwarded to a graphics driver DV that suitably effects display of the two images $V_p$, IM2 on one or more display devices DD.

It will be appreciated that operation of the layer definer LD may occur at an earlier phase than that of the rendering by renderer REN. The image processing system IPS may be arranged in a distributed environment with in particular the layer definer LD executed by one computing unit PU whilst the rendering takes place at another computing unit PU'. If the components, in particular renderer REN and layer definer LD, operate on different computing units (such as different servers or other computing units) in a Cloud architecture for example, it is envisaged in embodiments that these can still communicate through suitable communication interfaces over a suitable wireless or wired network.

Alternatively, all or substantially all, components of the IPS are integrated and run on the same computing unit. Specifically, the functionalities of the layer definer LD and of the renderer REN may be fused into a single computational entity. In such integrated embodiments, the layer definition operation of layer definer LD may take place during or concomitantly with the rendering operation REN. The layer definition may be integrated or form part of the rendering operation.

But again, alternatively, the two functions may be split time-wise so that the layer definition operation of layer definer LD occurs earlier than the rendering. The definition of the layer object LO may be provided as a suitable data structure, such as a binary mask, to the renderer RN. The function of the layer definer LD may be executed in a preparatory phase prior to the rendering phase by renderer REN and a specification of the defined layer object LO may be stored in a suitable data base. The stored object layer LO is retrieved on demand when the matching and rendering operation commences during the intervention, that is, when intra-operative imagery is received at input IN.

The rendering operation may be done in real-time as an on-line operation that occurs whilst the stream of intra-operative imagery IM2 is received at the image processor IPS at interface IN. The rendering by renderer REN is dynamically updated with each new frame captured in the stream of intra-operative images IM2. A gatekeeper unit (not shown) may check each frame whether there is a difference to an earlier frame exceeding a user definable threshold. A difference image may be formed from two consecutive frames to quantify said difference. If there is no such difference, the current rendering is maintained to safe CPU time. The re-computation of the rendering may be triggered only if the gatekeeper judges that the difference exceeds the threshold.

Figure 3:
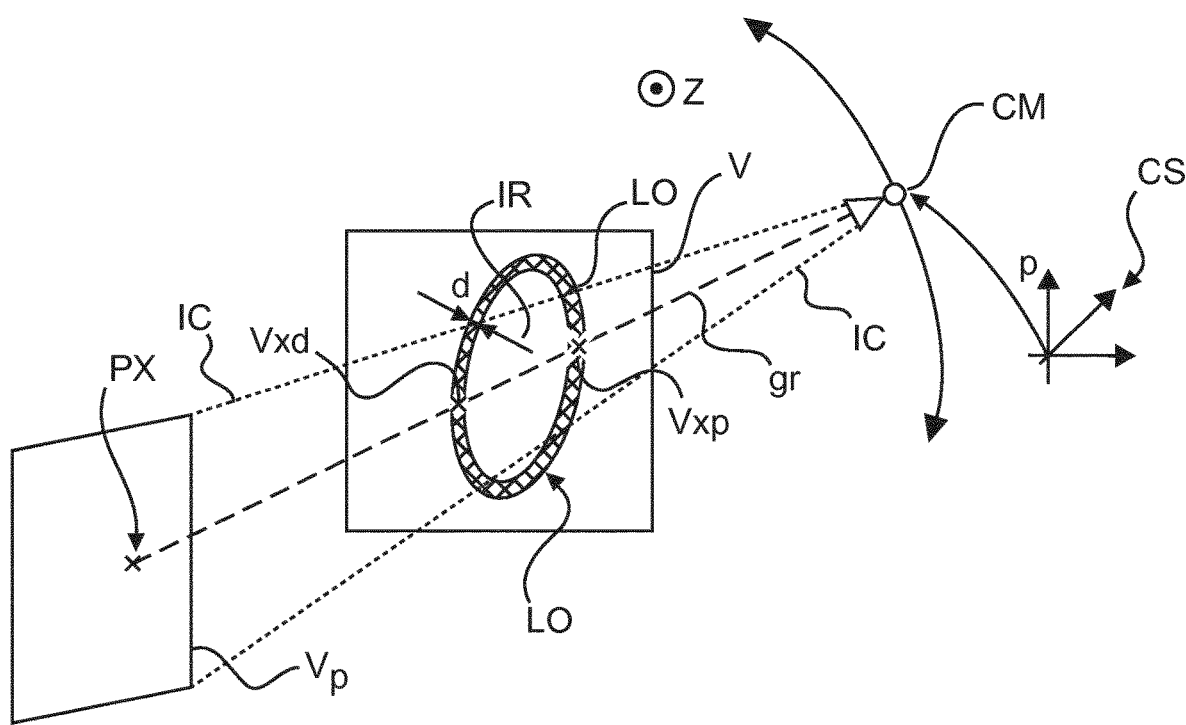
FIG. 3 illustrates a rendering operation of a part of an image volume.

Reference is now made to FIG. 3 which illustrates operation of renderer REN. Rendering is in general an operation where voxels in volumetric volume VL are processed to produce a preferably planar image that corresponds to view Vp of the volume, in particular of layer object LO, from a conceptual camera CM spatial position p in a virtual space in which volume Vp is embedded. Both, camera position and space can be represented as data stored in memory of computing unit PU. Rendering operation is preferably performed by a multi-core processor such as GPU (graphical processing unit) or TPU (tensor processing unit) or other. Position p of camera CM is schematically indicated by positional vector p defined in a common co-ordinate system CS in which the volume V is located.

View $V_P$ is a 2D image in an image plane. The view $V_P$ is computed by casting geometrical rays gr (only is shown in dashed lines in FIG. 3) from the conceptual camera position at p through the volume VL. The values of voxels that intersect a given geometrical ray gr are then sampled and processed according to a transfer function T to produce a respective image value for view $V_P$ at pixel position PX. Depending on a desired size of the image $V_P$ and the distance between the image plane and the camera position p, an image cone IC can be defined that encompasses all geometrical rays. The cone is schematically indicated as a pair or converging dotted lines. Only voxels in the volume that intersect image cone IC are considered when computing the pixels PX in the view $V_P$. Image values for all rays gr within the cone IC then form the view $V_P$.

As mentioned, a transfer function T processes the voxels that intersect a given geometrical ray gr in the rendering. In one embodiment the transfer function assigns a color or grey value and a transparency to a given voxel value. This can be achieved by forming a weighted sum of all voxel values along the given ray gr which may be formally written as:

$$T(gr) = \Sigma_{vxi \cap gr \neq \emptyset} I(Vxi) \cdot \lambda(Vxi) \cdot m(Vxi) \quad (1)$$

with I the indicator function of the mask,
λ the transparency weights and
m(.) the color or grey value mappings.

That is, each voxel value Vxi is multiplied by a weight λ that represents the transparency of the voxel value. In other words, transparency λ defines to what extent the respective voxel value contributes to the final image point PX at view $V_p$. A wide range of different transfer functions T to implement different rendering schemes are envisaged herein such as MIP, surface rendering, marching cube algorithms and others. The lung LG is shown in the volume in sagittal plane cross section.

As mentioned earlier, it is proposed herein to confine the rendering operations to voxels that lie in the above introduced layer LO having thickness d. The voxels in layer object LO represent lung tissue situated on the outer surface and up to a depth of d from surface S. The layer object LO thickness d corresponds to the penetration depth of the intra-operative imaging apparatus AI2 to be used. In embodiments this imaging apparatus is an endoscope the penetration depth of which is defined by the frequency and intensity of the interrogating light used to produce the imagery.

Voxels that lie in an inner region IR of layer object LO are essentially ignored in the rendering and so are, given a certain camera position p, distal voxels Vxd that are situated at the distal side of the layer object LO. It is only proximal voxels Vxp whose values contribute to the rendering. It will be appreciated that the concept of distal and proximal voxels changes with camera position p. Said differently, a camera position that is proximal with respect to a given camera position may be a distal voxel with respect to another camera position p'. A portion may be said to be "distal", if, given a camera position, the said portion would require a geometrical ray to intersect the layer object LO twice in order to pass through the said portion.

Voxels that lie outside the layer object LO and in a distal portion of the layer object LO are all ignored in the rendering given a camera position p. The voxels outside the layer objects are called non-layer voxels. These include in particular the voxels in the inner region IR that is surrounded by the object layer LO. One way to ensure that the distal voxels in the distal portion of the layer object LO and the voxels in the inner region IR are ignored is by setting their transparencies to opaque. This can be done by, for instance, multiplying the respective voxels with transparency factor λ=0 to essentially eliminate their contribution to the pixel PX in the plane of view $V_p$.

However, this is a matter of convention and other numerical schemes may be used to eliminate distal voxels and inner region voxels. The identities of voxels inside the layer object LO can be pre-defined by a layer definition operation implementable by the layer definer LD mentioned above. One way to do this is to define a binary mask. A binary mask is a data structure comprising "0" (numeric zeros) and "1" (numeric unity) that assigns the zeros and ones to respective voxel positions. The binary mask is hence a binary scalar field. In one mask embodiment, the renderer includes entries of the mask as factors into the transfer function T thereby automatically eliminating non-desired voxels outside the proximal layer object LO. These entries are represented as values of indicator function I(•) integrated in transfer function expression eq(1).

In another embodiment the layer object LO is pruned before rendering same from a given camera position P. In this embodiment the inner region IR and the distal portion of the layer object is simply discarded leaving only a partial portion of the object layer LO, namely the proximal one, that lies within the image cone IC to be rendered.

In yet another embodiment, because the penetration depth is known, the rendering terminates after given a number of voxels (that define a rendering length) along each geometrical ray. The rendering length may be computed from the known penetration depth (specifiable in a suitably length dimension, such as mm, cm or other) and the resolution of the imagery, the number of voxels that correspond to the penetration depth d. For rays gr that are not normal to the outer surface of the object layer, the rendering length may need to be adjusted by a factor, such as cos (a), a being an angle that measures the deviation from normal incidence.

Instead of outright ignoring non-layer voxels as described above, a fuzzy version of this embodiment is also envisaged. In this fuzzified embodiment, non-layer voxels and/or the distal portion voxels Vxd are being given by the renderer REN at least some contribution other than "0" but where at least the proximal voxels of the layer object LO are given a higher contribution than the non-layer voxels and/or the distal portion Vxd voxels.

A number of different embodiments for defining the object layer LO will be discussed in more detail below in particular at step S420 in FIG. 4 to which reference is now made.

Figure 4:
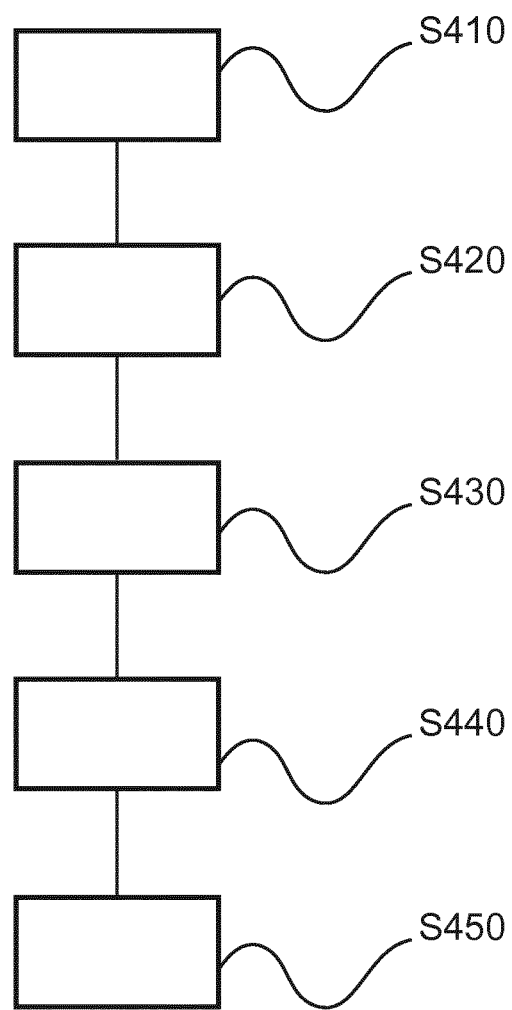
FIG. 4 shows a flow chart of image processing.

In particular, FIG. 4 shows a flow chart of an image processing method that underlies operation of the above mentioned imaging processing system IPS. However, it will be understood that the following method steps may also be understood as a teaching in their own right, not necessarily tied to the architecture of the image processing system IPS described above in FIG. 1.

At step S410 a pre-operative volume image VL of the patient, in particular of a lung LG of patient PAT, is received together with an intra-operative image IM2 acquired by an endoscope, ultrasound or other non-ionizing radiation based imaging modality. The intra-operative imagery and the pre-operative imagery are not necessarily received and processed at the same time.

First, the pre-operative imagery V is processed as follows with reference to next step S420 where a layer object LO is defined in the volume that represents in particular an outer surface of the lung LG and of further lung tissue situated up to d length units away and below the outer surface S. Accordingly, the layer object LO has a skin thickness that corresponds to d. The thickness d corresponds, that is, substantially equals, a penetration depth d of the radiation used by the intra-operative imaging modality, such as the endoscope. Alternatively, the thickness of the layer object LO may be less than the penetration depth. Voxels outside the object layer, that is those that are not situated within the thickness d do not form part of the object layer. In this sense, the layer objection may be conceptualized as a voxel sub-volume having a hollowed-out shell structure.

In one embodiment of step S420, various stages of lung tissue segmentations into sub-volumes is performed from which a mask image is derived that identifies the desired lung object LO having the requested thickness d. Because the resolution of the pre-operative imager IA1 is known and so is the theoretical penetration depth in a suitable length dimension that is, mm or cm, the required thickness may be readily translated into a corresponding sequence of voxels.

The said penetration depth can thus be expressed by a numbers of voxels rather than physical length dimension.

Figure 5:
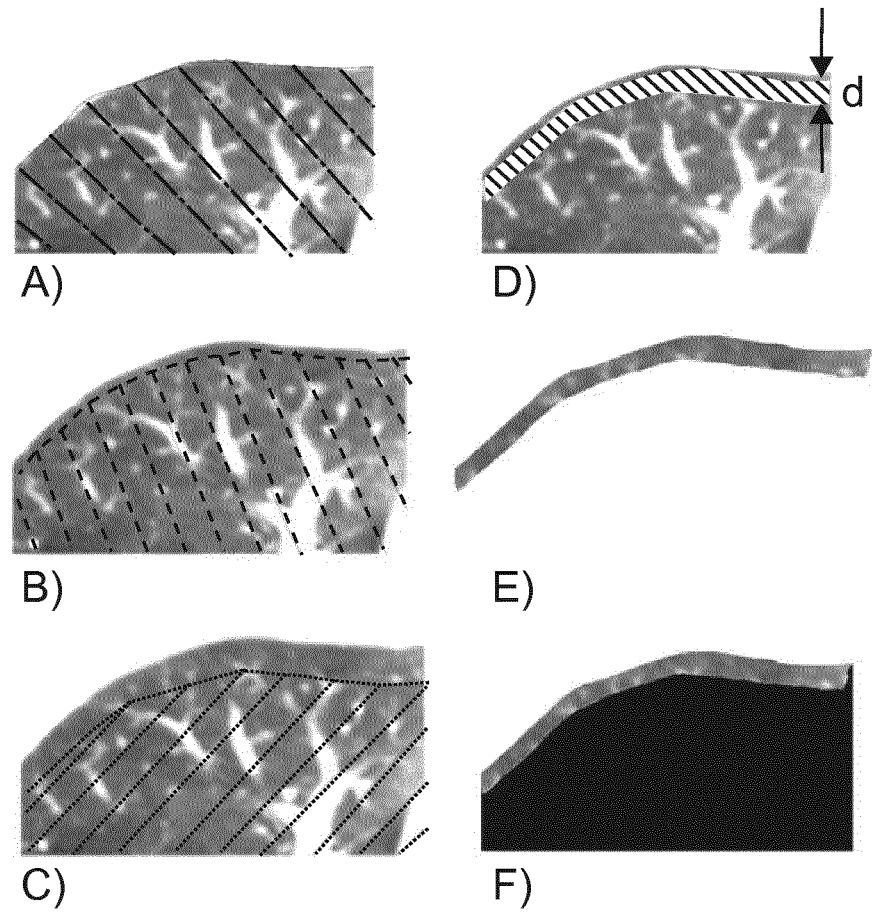
FIG. 5 shows intermediate and final results of image processing method.

These steps can be more easily appreciated with joint reference to FIG. 5 where exemplary intermediate imagery A)-F) is shown that emerges as intermediate and final results in certain sub-steps. In more detail, in embodiments step S420 includes the following sub-steps 1-5:

In sub-step 1 a segmentation of the lung L in the CT image is performed to output a lung object. This may be done by creating a lung mask, that assigns "1" or "0" to voxel positions. As per one convention, "1" indicates the respective voxel does represent lung whilst "0" indicates it does not. Other conventions may be used instead. We may refer to this mask as the "lung mask".

In sub-step 2, an image morphological erosion of the lung mask is performed to remove possible vestiges that represent non-lung tissue such as the unwanted thorax wall.

In sub-step 3, based on the penetration depth d of the inter-operative interrogating signal (e.g., (visible) light, IR, NIR or other) used by the inter-operative modality IA2, a second morphological erosion is performed to create a second lung mask, which is smaller than the lung mask obtained in sub-step 2.

In sub-step 4, the second mask is subtracted from the first mask to obtain a surface layer mask (a mask for the layer object). This differential mask includes voxels, which contribute to the visual appearance of the lung when exposed to the intra-operative imaging signal.

sub-step 5, the surface layer mask for the layer object LO is then used to mask those voxels of the original CT image, which contribute to the visual appearance.

FIG. 5A shows the segmentation of sub-step 1. This segmentation may still include remnants of the thorax wall which are then removed by the optional subsequent segmentation of sub-step 2 as illustrated in FIG. 5B. After the erosion or "hollowing out" operation of sub-step 3, the shell structure (in partial view) result is illustrated in FIG. 5C. The result of sub-step 4 is shown in FIG. 5D where the layer object LO is now emerging at the acquired penetration depth D and finally, after the last sub-step 5, a part of the layer object LO is shown in FIGS. 5E and 5F. The white portion in FIG. 5E and the black portion and white portions in FIG. 5F represent non-layer voxels that do not form part of layer object LO.

In addition to or instead of the first embodiment for lung layer object definition based on sub-steps 1-5, a further embodiment is envisaged herein that uses volume reformatting techniques. More particularly, in standard formatting, the planes of the slice images in volume VL are perpendicular to the imaging axis Z. This can be reformatted to generate, by reformatting algorithms, new slice images, each located in different image planes that are perpendicular to any desired direction Z', different from axis Z. Furthermore, the slice imagery may not necessarily be located in planes but may be located instead in respective curved surfaces. A series of curved surfaces is hence obtained that can be thought to propagate along any user definable normal direction (possibly different from Z) through the volume VL.

Such reformatting on curved surfaces within the initial volume VL are envisaged this second embodiment. In more detail, the second embodiment of step S420 includes in particular some or all of the following sub-steps as implementable by a hardware or software component such as the lung definer LD.

In the first sub-step 1, again, as before, a lung segmentation is performed to obtain a lung object as a sub-volume.

In sub-step 2, a point on the surface of the lung object within a certain neighborhood of a location of interest (lesion, e.g. tumor or other) is identified. The neighborhood, definable by a sphere or similar may be user definable by adjusting a diameter or radius of said sphere. In embodiments, the point on the surface may be the closest to the location of interest.

In sub-step 3, a curvilinear reformatted image volume is created in a certain neighborhood (e.g., a sphere) around the surface center point as identified at sub-step 2. This can be achieved by adopting a normal vector n of the lung wall at the center point, and then following the lung surface in a curved manner along orthogonal directions u and, v which are perpendicular to the normal vector n. The u, v then span a curvilinear reformat surface such that each point of the two-dimensional reformat is a part of the lung object surface. So, each point (u,v) in the reformat plane, can be mapped to a Cartesian point (x,y,z) in the image volume.

Now, having defined the curvilinear plane, in sub-step 4, one may sample the voxel values for each position (u,v) in the reformat plane for a few millimeters along a sampling ray with the normal direction n in the image volume until the visual penetration depth d has been reached. By 'sampling' as used herein is meant the process of looking up the value of the closest voxel in the (x,y,z) image volume grid, or interpolating the point value from a neighborhood of the closest voxels (e.g. tri-linear or cubic spline interpolation). All the values along each sampling ray are combined (see below) into a single brightness and color which is then rendered at position (u,v), the origin of the sampling ray, in the curvilinear reformat.

Turning now to the following steps S430 of layer object LO rendering and rendered view versus intraoperative image matching S440, these are executed in concert: in other words, a view or intra-operative image Vp on the defined lung object LO is rendered at step S430 in a manner so as to match S440 the current intra-operative image as received at step S410. The result of the rendering operation S430 is a virtual rendering of the lung surface S including in embodiments the pattern of superficial vessels and interlobular septa. In this manner, the pattern conferring features such as vessels and/or septa structures may be rendered at color coding clearly set off against the color coding of the remaining lung tissue that may be rendered in a preferably homogenous surrounding color (such as red or other). The pattern conferring structures such as vessels and septa structures may hence appear as discrete elements at least partly embedded in background that color codes the remaining tissue other than septa structures and/or vessels.

In the volume rendering of the layer object LO, preferably transparencies and colors are used that visually match the lung LG. For instance, for visible light, dark voxels in the volume may be rendered in a reddish fleshy, color, whilst bright voxels in the volume, usually corresponding to vessels, may be rendered in a dark color such as black or other. The rendering step S430 is performed as above described at FIG. 3. Non-layer voxels are ignored so the rendering step is capable of distinguishing between layer voxels∈LO and non-layer voxels∉LO. In addition to non-layer voxels, it is also the voxel in the distal portion of the layer LO that are ignored given a camera CM position p, as earlier explained in FIG. 3. Alternatively, the layer may be cut or pruned to remove, for each p, the relative distal portion. The pruned portion is then added back to LO when p is changed, and a new portion is the distal one and now this portion is removed, and so forth. In an alternative embodiment, instead of ignoring non-layer voxels and/or distal portion voxels, a fuzzification of this scheme is also envisaged as mentioned above in connection with FIG. 3.

The rendering step S430 may include rendering the curvilinear reformat. The rendering parameter p can be adjusted in interactive time while re-using the reformat volume. In either one of the above embodiments, an overlay rendering of the location of interest, such as of the tumor in question, may be performed at the appropriate (u,v) position in a different color, in order to indicate the position with respect to the surface pattern.

It can be taken into account during rendering that different tissues have different visibility in the spectral range of chosen.

In embodiments, additional information can be added to this rendering. This additional information may include planning data, such as planned cut planes, lesion position and lesion extent, and other. Since surgical planning as well as tumor segmentation is done on the original CT image, a registration of this rendering may not be necessary.

The matching operation S440 may be done by varying the camera position p along a conceptual circle surrounding the layer object LO whilst proceeding in suitable increments along this circle. Each view Vp so acquired is then compared to the intra-operative image IM2. The comparison may be based on a suitable similarity measure. Embodiments of similarity measure may be based on Euclidean-based norms such as the pixel-wise difference which is squared and summed and possibly weighted and/or normalized as required. Other similarity measures such as probability based, information theory measures (in particular entropy based) like mutual information, cross-entropy or discrete Kullback-Leibler divergence or others are included herein.

If a view $V_p$ is found that deviates from the currently provided intra-operative image by less than a user definable or fixed threshold, this view is then output at step S450 and displayed, preferably concomitantly with the intra-operative image IM2. The view $V_p$ and image IM2 may be display on a single display unit or, respectively, on two display units. Rather than proceeding step-wisely by stepping through a discrete set of camera image positions $p_j$ to so find the best view as described, the above may also be reformulated as an optimization problem in terms of an objective function dependent on parameter p. The objective function may then be optimized by any suitable optimization algorithm so as to optimize (such as minimize or maximize) the objective function. The view parameter defines in particular the position in space of camera CM and/or the width of image cone IC.

The objective function F(•) may in particular include as before a distance measure that measured a difference or deviation between the current intra-operative imagery IM2 and the parametrized view. The optimization problem may be formally written as:

$$\mathrm{argmin}_p F(p) = d(\mathrm{IM2}, V_p) + \mathrm{Reg} \qquad (2)$$

The parameter p is the variable to be optimized for, d(•,•) the distance measure, and Reg(•) an optional regularization term, possibly depending on p or IM2.

The matching may be performed by surface feature detection algorithm based on feature descriptors (FD). In embodiments, FD based algorithms envisaged herein include SIFT (scale invariant feature transform) or SURF or other Hough transform based variants thereof. Further embodiments, include GLOH or HOG. One advantage of these FD-based algorithms is that not specific correspondence pair need to be prescribed as such a feature pair approach is likely to fail in present contexts, where the lung is strongly deformed between the pre- and intra-operative phases due to inflation/deflation.

The operation of FD type algorithms can broadly be described as a two-step approach: there is, first, a detection step and, second, a feature descriptor extraction step. In the first step, a detection technique (e.g. blob detector) is used to detect a collection of locations (referred to herein as "candidate locations" or "candidate points") that are of potential interest. Image neighborhoods (e.g., n-dimensional-rectangles or n-dimensional spheres, n≥2) of the so collected candidate locations in the image are then analyzed in the second (feature extraction) step. In this analysis, feature descriptors are constructed that capture image structures of interest, such as particular image value distributions. The feature descriptors are preferably quantifiable in a suitable magnitude (or "strength") which is preferably invariant under rotation and/or scale. The feature descriptors from the rendered view Vp and the current intraoperative image IM2 are then compared to find, preferably the best possible, match. Even the best possible match of all respective candidate locations has certain residuals (discrepancies) left. The sum of these residuals of all matches then gives the value of the objective function F(•) for a single tested view $V_p$. The matching process is repeated for all tested views $V_p$, in order to find the optimal views $V_p$.

In the matching of the proposed method, the lung surface rendering Vp may essentially be warped so as to match the current intra-operative image, such as the 2D endoscope image. One possible embodiment to determine the best warping is to match feature point pairs, as described above. However, another embodiment work can work entirely without FD-based point pairs, rather with so called non-parametric 2D image registration. The 2D image registration determines a smooth displacement vector field such that the two images (Vp and IM2) can be overlaid with the highest possible e.g. mutual information or cross-entropy. This is then used as the value for the objective function F(.). The optimal warping vector field is determined under certain regularizing boundary condition, such as smoothness and minimum bending energy (e.g. so-called thin plate splines). In the proposed matching, it may hence be not necessary to extract feature point pairs as may be required in some current image registration based approaches.

However, other embodiments, not necessarily automatic as the above, but manual or semi-manual are also envisaged. For instance, the user simply scrolls through the different view positions to adjust the view that best fits the currently shown inter-operative imagery. In this embodiment, for instance the viewer changes the camera position and effects respective renderings for instance by touch screen action performing gestures such as a rotation or otherwise on a touch screen on which the current rendering is displayed. A pointer tool such as a computer mouse may be used instead to trigger the various renderings until the best match is found based on the provisional judgment by the operator. These manual or semi-automatic embodiments may then include matcher M or the matcher may still be present and operates the user to find the best matching view to be rendered. A visual or audio indication may be issued to indicate that a match has been found. For instance, a border portion of the rendering Vp as displayed on device DD may flash or change color to indicate the best match. Alternatively or in addition, text may be displayed such as "MATCH" or other once match has been found.

In either one of the above described embodiments, planning data may be automatically overlaid onto the intraoperative image and/or the rendered view Vp, e.g. during VATS. During the intervention, the user (e.g., surgeon) has access to the rendering Vp and, preferably to additional information from a pre-operative planning phase. The user may then mentally match ("mental registration") surface structures, which he or she can see directly on the real lung, with the rendering. He can thus perform the intervention according to the planning, e.g. cutting along the planned cut lines. Surgical planning data, e.g. cut lines, may be overlaid on the intra-operative image. Often this 2D surface information is sufficient, such as for a wedge resection. If 3D planning information is necessary, a biomechanical model of the lung deflation can be used for the 3D matching of the lung based on measured position of surface features in space.

Figure 6:
FIG. 6 shows an exemplary rendering of a human lung.

FIG. 6 shows an exemplary rendering Vp obtained by the first embodiment of step S420. As can be seen, superficial vessel structures are clearly visible in the rendering of the lung object LO.

In all the embodiments, although non-layer voxels are ignored, in embodiment the user may still have the option to request deeper lung structures. These may then be displayed in alternation with the rendering of the layer object or in addition thereto. Further anatomy may also be shown in addition to the layer object LO rendering such as exemplary illustrated in FIG. 6.

In the endoscopic embodiment, instead of using a detector device that is sensitive in the visible spectrum, light in other parts of the spectrum may be used instead. For instance, in embodiments, Near-InfraRed (NIR) light is used as this has the advantage that its penetration depth d in tissue is higher than it is in visible light. Thus, NIR images hence are capable of capturing additional features, thus leading to better feature matching later on.

In order to increase contrast one can use narrowband IR light (instead of white light) e.g. by using narrowband IR LEDs for illumination.

Figure 7:
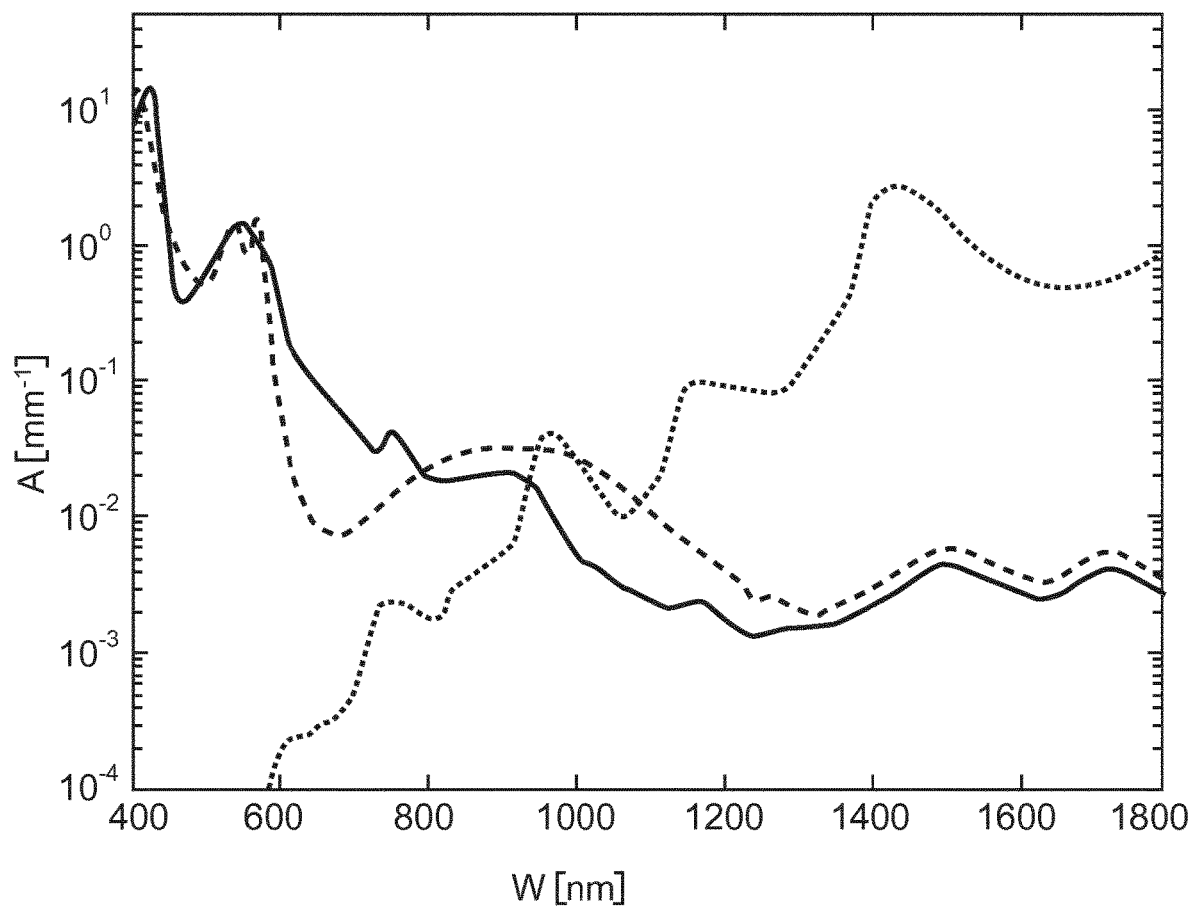
FIG. 7 illustrates spectral absorption curves for different materials.

Ideally the wavelength used is matched with absorption maxima of important structures. FIG. 7 depicts the absorption curves of water and haemoglobin in the visible and NIR region. There are clear absorption peaks that can be used to detect blood vessels with a high contrast. Because the absorption curve of oxygenized and deoxygenized haemoglobin differs, it is also possible to discriminate veins from arteries. This spectral imaging capability may be used to confer, in the rendering Vp or in the visualization of the endoscopic image IM2, different contrast or color to veins and arteries, respectively. Vessels are hence differentiated in the view $V_p$ and/or in the intraoperative image IM2 into arteries and veins based on prevailing materials present during the imaging, such as hemoglobin in oxygenized and deoxygenized form, respectively.

Various further refinements and additional features are also envisaged in embodiments. The surgeon/radiologist may use the preoperative image volume IM1 to identify or localize a lesion or other feature of interest in this image.

The rendering $V_p$ may be enhanced by including further anatomic features, in addition to the vessels and/or septa objects, such as lymph nodes.

The surgeon/radiologist can plan the intervention, e.g. by defining lesion margins or cut lines for a wedge resection. The position of important landmarks (lesion, margins, cut lines, etc.) may be estimated ("mental registration") based on the identified surface features. Hints for the surgeon's orientation, e.g. the position of the lesion or the planned cut lines, may be overlaid as graphical components on the intra-operative image IM2 and these components may then be included in the rendering.

The components of the image processing system IPS may be implemented as software modules or routines in a single software suit and run on a general purpose computing unit PU such as a workstation associated with the imager IA1 or IA2 or a server computer associated with a group of imagers IA1, IA2. Alternatively, the components of the image processing system IPS may be arranged in a distributed architecture and connected in a suitable communication network.

Alternatively, some or all components may be arranged in hardware such as a suitably programmed FPGA (field-programmable-gate-array) or as hardwired IC chip.

One or more features of the IPS disclosed herein may be configured or implemented as/with circuitry encoded within a computer-readable medium, and/or combinations thereof. Circuitry may include discrete and/or integrated circuitry, application specific integrated circuitry (ASIC), a system-on-a-chip (SOC), and combinations thereof, a machine, a computer system, a processor and memory, a computer program.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium (in particular, but not necessarily, a non-transitory medium), such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments.

Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

As used herein, the term "or" should be interpreted as a disjunctive "or." Further, the term "or" and the term "and" when prefaced by the term "at least one of" or the term by "one or more of" should be interpreted as a disjunctive list such that, for example, a list of "at least one of A or B" or a list of "one or more of A and B" or a list of "A or B" should be interpreted to include either A or B, one of A and one of B, a combination of one or more of each of A and B; both A and B, or combinations of one or more of A and B, and such other combinations as relevant to the recited list or terms consistent with the corresponding description in the specification.

The invention claimed is:

1. A system for image-based navigation, the system comprising:
   an input interface configured to receive i) at least a part of a three-dimensional (3D) image volume based on image data of a lung of a subject acquired pre-operatively by a first imaging modality and ii) a second image the lung in a deflated state dynamically acquired by a second imaging modality during an operation; and
   a processor configured to:
   define, in the 3D image volume, a layer object that includes a pattern on a surface of the lung that is representative of at least one of a lung vessel or a septum,
   identify the pattern in the second image of the lung,
   match the second image of the lung in the deflated state to the 3D image volume based on the pattern,
   render a rendering view of the 3D image volume matched to the second image, and
   display a visualization of the rendering view.

2. The system of claim 1, wherein the processor is configured to confine rendering of the layer object to a part of the layer object, or the processor is configured to set voxels within the layer object to provide a higher contribution to pixels in the rendering view than voxels outside the layer object.

3. The system of claim 1, wherein the processor is configured to define a thickness of the layer object based on a penetration depth of an interrogation signal of the second imaging modality.

4. The system of claim 1, wherein the processor is configured to define the layer object by segmenting the lung into sub-volumes and deriving a mask image from the sub-volumes based on a defined thickness for the layer object.

5. The system of claim 1, wherein the processor is configured to define the layer object using a volume reformatting technique.

6. The system of claim 1, wherein the processor is configured to render the pattern with color-value or grey-value encoding that is different from a surrounding in which the pattern is at least partly embedded.

7. The system of claim 1, wherein the processor is configured to set a transparency of the rendered layer object to occlude a distal portion of the layer object or the processor is configured to prune the layer object to exclude the distal portion from being rendered.

8. The system of claim 1, further comprising a display device interface configured to affect the display of the visualization of the rendering view and the second image on at least one display device.

9. The system of claim 1, wherein the processor is configured to color-value or grey-value encode vessels of the layer object so that veins are differentiated from arteries in the visualization of the rendering view, based on oxygenized hemoglobin or deoxygenized hemoglobin being present in a corresponding portion of the lung during imaging of the lung.

10. The system of claim 1, further comprising at least one of the first imaging modality, the second imaging modality, or at least one display device.

11. A method of image-based navigation, the method comprising:
    receiving i) at least a part of a 3D image volume of a lung of a subject based on image data acquired pre-operatively by a first imaging modality and ii) a second image of the lung in a deflated state dynamically acquired by a second imaging modality during an operation;
    defining, in the 3D image volume, a layer object that includes a pattern on the surface of the lung that is representative of a lung vessel or a septum;
    identifying the pattern in the second image;
    matching the second image of the lung in the deflated state to the 3D image volume based on the pattern;
    rendering a rendering view of the 3D image volume matched to the second image; and
    displaying a visualization of the rendering view.

12. The method of claim 11, further comprising confining rendering of the layer object to at least a part of the layer object or setting voxels within the layer object to provide a higher contribution to pixels in the rendering view than voxels outside the layer object.

13. A non-transitory computer readable medium having stored thereon instructions, which, when being executed by at least one processor, cause the at least one processor to:
    receive i) at least a part of a 3D image volume of a lung of a subject based on image data acquired pre-operatively by a first imaging modality and ii) a second image of the lung in a deflated state acquired dynamically by a second imaging modality during an operation;

define, in the 3D image volume, a layer object that includes a pattern on the surface of the lung that is representative of at least one of a lung vessel or a septum;

identify the pattern in the second image;

match the second image of the lung in the deflated state to the 3D image volume based on the pattern;

render a rendering view of the 3D image volume matched to the second image; and display a visualization of the rendering view.

14. The method of claim 11, further comprising defining a thickness of the layer object based on a penetration depth of an interrogation signal of the second imaging modality.

15. The method of claim 11, further comprising defining the layer object by segmenting the lung into sub-volumes and deriving a mask image from the sub-volumes based on a defined thickness for the layer object.

16. The method of claim 11, further comprising defining the layer object using a volume reformatting technique.

17. The method of claim 11, further comprising rendering the pattern with color-value or grey-value encoding that is different from a surrounding in which the pattern is at least partly embedded.

18. The method of claim 11, further comprising setting a transparency of the rendered layer object to occlude a distal portion of the layer object or pruning the layer object to exclude the distal portion from being rendered.

19. The method of claim 11, further comprising color-value or grey-value encoding vessels so that veins are differentiated from arteries, in the visualization of the rendering view, based on oxygenized hemoglobin or deoxygenized hemoglobin being present in a corresponding portion of the lung during imaging of the lung.

* * * * *